United States Patent [19]

Imre et al.

[11] Patent Number: 4,908,507
[45] Date of Patent: Mar. 13, 1990

[54] PROCESS AND APPARATUS FOR THE INTEGRAL OPTICAL EXAMINATIONS OF DAMAGING MECHANICAL STRESSES IN THE BOTTOM-PART OF BOTTLES AND HOLLOW GLASSWARE

[75] Inventors: Dobi Imre, Orosháza; Péter Karabélyos, Budapest; János Kugyela; Béla Tóh, both of Orosháza, all of Hungary

[73] Assignee: Ovegipari Muvek, Budapest, Hungary

[21] Appl. No.: 256,155

[22] Filed: Oct. 7, 1988

Related U.S. Application Data

[63] Continuation of Ser. No. 22,796, Mar. 6, 1987, abandoned.

[30] Foreign Application Priority Data

Mar. 10, 1986 [HU] Hungary .............................. 1001/86

[51] Int. Cl.$^4$ .............................................. G01H 9/04
[52] U.S. Cl. .................................. 250/223 B; 356/240
[58] Field of Search ........................... 250/223 B, 225; 356/239, 240; 209/526

[56] References Cited

U.S. PATENT DOCUMENTS 3,770,969  11/1973  Ansevin et al. ................. 250/223 B
3,963,348   6/1976  Nakatani et al. ................ 250/223 B
4,026,656   5/1977  Kusz et al. ........................ 356/240
4,547,067  10/1985  Watanbe ............................ 356/240

Primary Examiner—Edward P. Westin
Assistant Examiner—Khalid Shani
Attorney, Agent, or Firm—Schweitzer & Cornman

[57] ABSTRACT

The invention relates to a process for the integral optical examination of damaging mechanical stresses arising in the bottom-part of bottles and hollow glasswares. In accordance with the process the bottom-part of the glasses/bottles/is illuminated with a light bundle from the mouth, the cross-sectional intensity distribution is controlled by the aid of a light bundle with predetermined angle of aperture, with the integral optical system the bottom is illuminated with a light with quasi-homogeneous intensity. The passing light is modulated and led into the photodetector, the signal of which is analysed through a band-filter. The invention includes the apparatus for the implement of the process according to the invention. The apparatus has a laser (1), a laser bundle (2) emitted therefrom, a polar filter (3), connected with a light-chopper (4), a bundle stretcher consisting of the collecting lenses (5,6), the diaphragm (8), a polar filter (14) and the photodetector (15).

12 Claims, 1 Drawing Sheet

PROCESS AND APPARATUS FOR THE INTEGRAL OPTICAL EXAMINATIONS OF DAMAGING MECHANICAL STRESSES IN THE BOTTOM-PART OF BOTTLES AND HOLLOW GLASSWARE

This is a continuing application of U.S. Ser. No. 022,796, filed on Mar. 6, 1987, now abandoned.

FIELD OF THE INVENTION

The invention relates to an optical testing method and apparatus implementing the process of the invention, by the aid of which damaging mechanical stresses of the bottoms of bottles and other hollow glassware can be detected, measured and qualitatively classified.

BACKGROUND OF THE INVENTION

Liquids, such as products of the food processing industry are generally stored in glasses and bottles. Useful life of such glasses depends considerably on the extent of any damaging stresses in the glass. Stress-freedom of glasses filled under pressure is of special importance, to minimize the risk of explosion. Production technology of glassware such as bottles, by pressing or blowing, often results in damaging mechanical stresses. Detection and control of mechanical stresses in the bottom of the glassware represent a most important task both for reducing waste and obtaining maximum operative safety. Accordingly, a testing-qualifying method and apparatus therefor are needed, which is suitable for the final qualitative control of the glasses and thus it is imperative to develop a method for quick measurement and quality control The aim of the invention is to perform quality control of the stresses raised in glass bottles, etc. on the basis of objective criteria and with a high sensitivity, by detecting the index of birefringence at the bottom of hollow glassware.

Presently this task is solved by a conventional polariscope, stress-testing apparatus, in the glass industry.

Function of the apparatus is based on the phenomenon of the tension-caused birefringence. Under the effect of mechanical stresses the glass, which is originally optically isotropic, becomes double-refractive or birefringent. That means that distribution of the refractive index is not spherical but ellipsoidal. State of polarization of the light passing through the glass which became birefringent, changes in comparison to the state of polarization of incident light, that means that generally the linearly polarized light will be converted into elliptically polarized light. Thus the glass to be tested is illuminated with linearly polarized white light from the bottom of the glass, through partly a light-diffuser screen permeable to light is used for homogenizing the cross-sectional intensity distribution of the illuminating light beam, followed by a polar filter with a large diameter /30 to 40 cm/. The glass is placed into the path of the light thus produced and the axis of the rotation of the glass is parallel with the illuminating light bundle. The light passing through the bottom of the glass bottle is detected visually through the second polar filter (analyzer) so that by rotating the axis of the glass object visible parts of the bottom can be examined through the mouth of the glass bottle. Colored strips (isochromates) become visible after the analyzer. These are characteristic of the stress distribution in the bottom of the bottle.

This prior art is described in greater detail e.g. by Miklos Vermes: Polar light, Technical Publishers, 1967; Manual of Glass Industry, Technical Publishers, Hungary 1964. Many methods are known for testing the mechanical stresses in optical materials. In one of these monochromatic planar polar incident light is used instead of white light, while a system of black strips is formed after the analyzer. This characterizes the planar distribution of the stresses. That test is performed in a most complicated fashion by qualified visual observation and analysis.

Summing up all known methods it can be stated, that:
1./ Detection is subjective, in particular the detection of low stresses, where a little color displacement increases uncertainty in measuring.
2./ Evaluation is slow, and there is no way to display the measured stress distribution.
3./ These known methods are not suitable for producing a qualifying "measuring index" integrally characterizing the whole area of the glass bottom.
4./ One cannot examine the entire area of the bottom at the same time by means of the usual parallel or diffuse illuminating methods in the case of bottles with a small neck diameter.
5./ At low stresses the detectable light intensity is extraordinarily small, and the smallest detectable stress changes in dependence of the extent of polarization, monochromacity of the light source, and the ambient light.

Thus, the known methods do not solve the problem.

DESCRIPTION OF THE INVENTION

Our invention is based on the recognition of the following factors:
The bottoms of the glass bottles are to be illuminated from the mouth of the bottle with a conically shaped light bundle having a predetermined aperture angle to achieve simultaneous illumination of the whole bottom and to avoid the illumination of the sidewall of the bottle.
Laser is used as a light source. The bundle of this source is collimated for producing light cones which are fitted to bottles with different heights.
Linearly polarized laser beam is used, followed immediately by a polarizing filter, the transmission direction of which is parallel with the polarization plane of the laser bundle to reduce apolar or partly polar noise-light coming from the discharge tube of the laser, or from the ambiance, and to increase sensitivity.
Cross-sectional intensity distribution of the Gaussian-distribution of the laser bundle is so influenced by the optical system that the light cone should uniformly illuminate the whole area of the bottom with a homogeneous intensity to assure simultaneous integrated measurement throughout the entire bottom area of the bottle.
The light passing through the entire surface of the bottom is detected by one single photodetector having been arranged behind the analyzer for integral measurement.
Intensity of the laser bundle is modulated in time by a light chopper signal of the photodetector and this is analyzed through a band-pass filter having been tuned to the modulation frequency of the light. This increases sensitivity by reducing the effect of ambient noise-light.

BRIEF DESCRIPTION OF THE DRAWING

The drawing is a schematic representation of the preferred embodiment of the invention.

DESCRIPTION OF A PREFERRED EMBODIMENT

Figure 1:
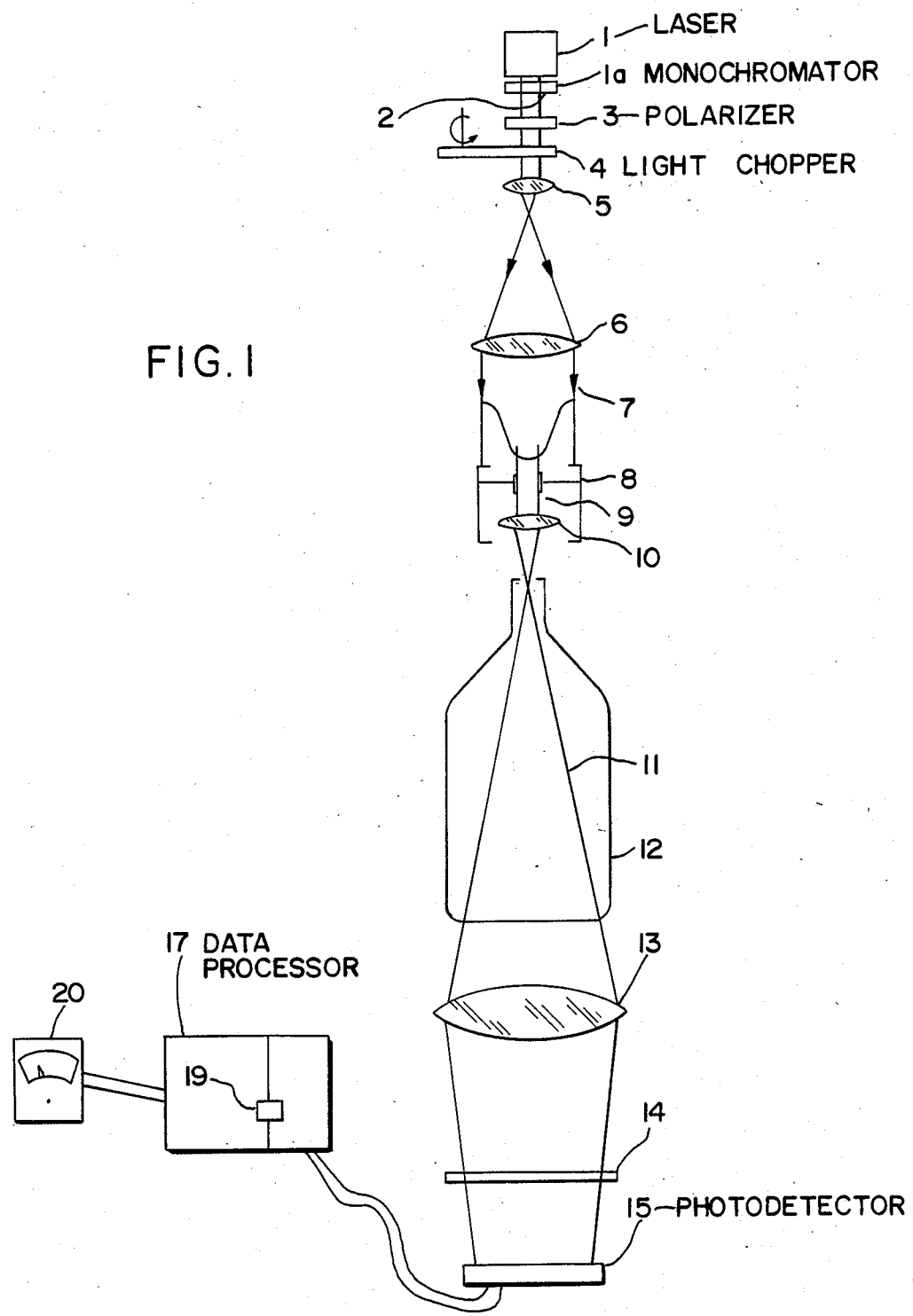

A preferred embodiment is described with reference to the sole FIGURE of the drawing which is a schematic representation of the measuring arrangement.

A laser 1 emits an exiting linearly polar light bundle 2. This passes through a polarizing filter 3. The laser itself can be gas, semiconductor or a solid state laser, radiating at any preselected wavelength. If the laser is of a type which emits simultaneously light of several discrete wavelengths, a monochromatic laser bundle 2 can be obtained by the use of monochromator 1a, such as a grid, a prism, or any other disperse optical element. Direction of transmission of the polar filter 3 is adjusted to run parallel with the polarization plane of the laser bundle 2. In this case the extent of polarization of the laser bundle 2 will increase and the intensity of the non-monochromatic apolar light coming from the discharge tube of the laser will be considerably reduced.

A light-chopper 4 is disposed after the polar filter 4 in the direction of travel of the light bundle 2. The light chopper modulates the intensity of the laser bundle 2 as a function of time. The light-chopper 4 can be a rotating chopper disc, an electromagnetically moved knife-edge, acustical-optical intensity modulator, or any other modulator, or any other modulator which does not affect the state of polarization of the light bundle.

The light bundle 2 is led into a beam expander arrangement after the light-chopper 4. In this preferred embodiment this consists of collecting lenses 5 and 6. The beam expander fulfils a double task. Partly it increases the diameter of the incident diameter (about 1 mm) light bundle by a factor of 15–20, and partly it reduces angular divergence of the light bundle to the same extent. The laser bundle 7 leaving the beam expander arrangement will remain parallel even within a large distance such as about 1 m, if the distance of the lenses 5, 6 of the arrangement is properly adjusted. A diaphragm 8 is arranged next in the path of the light bundle. The diameter of the diaphragm can be adjusted continuously or in stages. The center of the diaphragm coincides with the central beam defining the axis of the light bundle. As represented in the drawing, the light rays in the cross section are of a Gaussian intensity distribution. The diaphragm allows passage of only those rays, which are disposed in the vicinity of the axis of the bundle or the more uniform part of the Gaussian curve. Therefore the intensity distribution of the light bundle 9 that passes through the diaphragm will be nearly uniform, while its diameter can be varied.

The optics after the diaphragm 8 are represented by the collecting lens 10. This collecting lens 10 focuses the parallel light bundle 9 to produce an illuminating light cone 11, which illuminates the entire bottom of the bottle 12 from the neck of the bottle. Thus the light cone does not touch the sidewall of the bottle. Due to the light reflections from lateral frictional direction, light beams arrive at the bottom of the bottle having a low extent of polarization. This can decrease the sensitivity of the apparatus. The focal length of the collecting lens 10 is small, 10 mm, and it is so spaced from the diaphragm that the optical geometric image of the diaphragm 8 coincides with the plane of the bottom of the bottle. The diaphragm 8 and the collecting lens 10 are installed in a common housing (not shown) and can be moved together along the axis of the laser bundle 7. Illuminating cones with different angles of aperture can thus be produced by varying the diameter of the diaphragm by displacing it. These illuminating cones will well match shapes of the different bottles and hollow glass objects to be examined.

The light passing through the bottom of the bottle is collected by a collecting lens 13 and is then passed through an analyzer polarizing filter 14 to a photodetector 15. The focal length of the collecting lens 13 and the distance measured from the bottom of the bottle are chosen so that the aperture of the collecting lens 10 should be imaged onto the light receiving plane of the photodetector 15.

Transmission through the analyzer polarizing filter 14 should be oriented normal to the direction of the plane of polarization of the polarizer 3. If the bottle is free of stresses no light arrives at the photodetector 15. When the bottom of the bottle or other glass object contains stresses, the light incident onto the polar filter 14 will be elliptically polarized and, accordingly, light is detected by the photodetector 15. It can be demonstrated numerically and confirmed by experiments, that the amplitude of the light pulses arriving at the photodetector is proportional according to $$T = \tfrac{1}{2}\left[ 1 - \cos \frac{2\pi}{\lambda_o} c\sigma d \right]$$

wherein
T means the transmission of the optical system,
$\lambda_o$ means wavelength of the laser,
c means stress-optical constant,
$\sigma$ means the unidirectional mechanical stress and
d means the thickness of the glass bottom For the expression the monovalent monotonous increasing function of $\sigma$. The magnitude of the signal of the photodetector may serve as a basis of qualification.

The output of the photodetector 15, can be connected to an electronic data processing unit 17, in which a band-pass filter 19 is tuned to the modulation or light copping frequency. In that case the amplitude of the sine wave signal at the filter output is independent of the ambient light, because that generates a DC signal. The pulses of the photodetector are led to the band-pass filter 19 and there after the magnitude of the output signal of the filter is measured by a voltage meter 20. Quality control takes place on basis of the magnitude of the voltage measured.

We claim:

1. A process for the integral optical examination of mechanical stresses in the bottom of a transparent container, which comprises the steps of;
    (a) polarizing the output light beam of a light source;
    (b) substantially uniformly, periodically, optically interrupting the polarized light beam at a preselected frequency;
    (c) optically expanding the diameter of said light beam;
    (d) reducing the angular divergence of said expanded light beam;
    (e) sampling a substantially uniform intensity portion of said light beam;

(f) substantially uniformly illuminating the bottom of said container with said sampled light beam portion through the mouth of the container;

(g) collecting the light beam after it passes through the bottom of said container;

(h) passing the collected light beam through an analyzing polarizing filter; and (i) quantitatively determining the stress characteristics of the bottom of said container.

2. The process of claim 1, wherein said step (e) comprises passing said light beam through a diaphragm and said step (f) comprises imaging the diaphragm onto the bottom of said container.

3. The process of claim 1, wherein step (g) comprises imaging the bottom of the glass object onto a photodetector employed in step (i).

4. The process of claim 1, wherein step (i) is carried out as a function of the periodicity of interrupting in said step (b).

5. The process of claim 1, further comprising the step of monochromating the output of said light source.

6. Apparatus for the integral optical examination of mechanical stresses in the bottom of a transparent container, which comprises, in successive order a light source for emitting a light beam having a diameter and an angular divergence, means for polarizing said light light beam, a modulator for modulating the pulse frequency of said light beam, means for optically expanding the diameter of said light beam and for reducing the angular divergence thereof, means for sampling a substantially uniform intensity of the cross section of said light beam, means for substantially uniformly illuminating the bottom of said transparent container without illuminating side walls of said container, means for collecting the light beam, analyzer polarizing means for filtering out that part of the light beam having a plane of polarization perpendicular to the plane of polarization of said analyzer polarizing means, a photodetector for converting into an electrical signal the light beam passed by said analyzer polarizing means, means for substantially filtering out the effect of ambient light from said electrical signal, and means for correlating the strength of said signal to stresses in the bottom of said transparent object.

7. The apparatus of claim 6, wherein said light source is a laser.

8. Apparatus according to claim 6, wherein said modulator is a light chopper rotating at a preselected speed.

9. The apparatus of claim 6, wherein said optically expanding- and for angular divergence-reducing means comprises two lenses arranged in succession.

10. The apparatus of claim 6, wherein said means for substantially equalizing the intensity of said light beam comprises a diaphragm.

11. The apparatus of claim 6, wherein said means for substantially uniformly illuminating the bottom os said transparent container, comprises a lens arranged in a fixed relationship with said means for substantially equalizing the intensity the cross section of said light beam.

12. The apparatus of claim 6, wherein said means for substantially filtering out the effect of ambient light, comprises a band-pass filter tuned substantially to the frequency of the modulator.

* * * * *